(12) United States Patent
Gallagher et al.

(10) Patent No.: US 11,292,371 B2
(45) Date of Patent: Apr. 5, 2022

(54) SEAT ASSEMBLY

(71) Applicant: Lear Corporation, Southfield, MI (US)

(72) Inventors: David Gallagher, Sterling Heights, MI (US); Francesco Migneco, Saline, MI (US)

(73) Assignee: Lear Corporation, Southfield, MI (US)

(*) Notice: Subject to any disclaimer, the term of this patent is extended or adjusted under 35 U.S.C. 154(b) by 20 days.

(21) Appl. No.: 15/930,865

(22) Filed: May 13, 2020

(65) Prior Publication Data

US 2021/0354605 A1 Nov. 18, 2021

(51) Int. Cl.
*B60N 2/56* (2006.01)
*B60N 2/90* (2018.01)
*B60N 2/02* (2006.01)
*G16H 50/20* (2018.01)
*B60N 2/66* (2006.01)

(52) U.S. Cl.
CPC ........ *B60N 2/5678* (2013.01); *B60N 2/0244* (2013.01); *B60N 2/665* (2015.04); *B60N 2/914* (2018.02); *B60N 2/976* (2018.02); *G16H 50/20* (2018.01); *B60N 2002/0268* (2013.01)

(58) Field of Classification Search
CPC ...... B60N 2/5678; B60N 2/665; B60N 2/976; B60N 2/914; B60N 2/0244; B60N 2002/0268
USPC ......................................... 297/180.1, 180.12
See application file for complete search history.

(56) References Cited

U.S. PATENT DOCUMENTS

| 5,769,490 A | 6/1998 | Falzon |
| 6,056,360 A | 5/2000 | Schneider |
| 6,079,485 A * | 6/2000 | Esaki ................. B60H 1/00285 297/180.1 X |
| 6,088,642 A | 7/2000 | Finkelstein et al. |
| 6,088,643 A | 7/2000 | Long et al. |
| 6,098,000 A | 8/2000 | Long et al. |
| 6,179,378 B1 * | 1/2001 | Baumgartner ......... B60N 2/002 297/180.12 X |
| 6,345,839 B1 | 2/2002 | Kuboki et al. |
| 6,353,207 B1 | 3/2002 | Burt |
| 6,506,153 B1 | 1/2003 | Littek et al. |
| 6,559,422 B2 | 5/2003 | Burt |

(Continued)

FOREIGN PATENT DOCUMENTS

| CN | 2855822 Y | 1/2007 |
| CN | 203186154 U | 9/2013 |

(Continued)

OTHER PUBLICATIONS

Co-pending U.S. Appl. No. 16/821,128, filed Mar. 17, 2020.

(Continued)

*Primary Examiner* — Rodney B White
(74) *Attorney, Agent, or Firm* — Fishman Stewart PLLC

(57) ABSTRACT

A seat assembly may include a seat having a seat base and a seat back, a temperature control unit disposed at least partially in the seat back, and/or an ECU connected with the temperature control unit. The ECU may be configured to receive an input related to (i) a first state corresponding to symptoms and/or discomfort associated with dysmenorrhea and/or (ii) a second state corresponding to symptoms and/or discomfort associated with sciatica. The ECU may be configured to operate the seat assembly according, at least in part, to the input.

20 Claims, 6 Drawing Sheets

(56) References Cited

U.S. PATENT DOCUMENTS

| | | |
|---|---|---|
| 6,682,494 B1 | 1/2004 | Sleichter, III et al. |
| 6,908,152 B2 | 6/2005 | McMillen |
| 7,011,369 B2 | 3/2006 | Massara et al. |
| 7,083,232 B2 | 8/2006 | Frank |
| 7,083,233 B2 | 8/2006 | Massara et al. |
| 7,152,920 B2 | 12/2006 | Sugiyama et al. |
| 7,201,446 B2 | 4/2007 | Massara et al. |
| 7,219,923 B2 | 5/2007 | Fujita et al. |
| 7,267,652 B2 | 9/2007 | Coyle et al. |
| 7,303,231 B2 | 12/2007 | Frank |
| 7,314,451 B2 | 1/2008 | Halperin et al. |
| 7,417,536 B2 | 8/2008 | Lakshmanan et al. |
| 7,688,582 B2 * | 3/2010 | Fukazu .................. B60L 50/66 297/180.1 X |
| 7,731,279 B2 | 6/2010 | Asada et al. |
| 7,808,395 B2 | 10/2010 | Raisanen et al. |
| 7,828,050 B2 * | 11/2010 | Esaki .................. B60N 2/5635 297/180.1 X |
| 7,862,119 B2 | 1/2011 | Schafer et al. |
| 7,866,755 B2 | 1/2011 | Okano |
| 7,900,736 B2 | 3/2011 | Breed |
| 7,967,379 B2 | 6/2011 | Walters et al. |
| 7,967,381 B2 | 6/2011 | Sugiyama |
| 8,341,786 B2 | 1/2013 | Oexman et al. |
| 8,444,558 B2 | 5/2013 | Young et al. |
| 8,616,654 B2 | 12/2013 | Zenk et al. |
| 8,618,451 B2 * | 12/2013 | Kunisada ................ H01C 3/06 297/180.12 X |
| 8,706,204 B2 | 4/2014 | Seo et al. |
| 8,710,784 B2 | 4/2014 | Meyer et al. |
| 8,725,311 B1 | 5/2014 | Breed |
| 8,794,707 B2 | 8/2014 | Bocsanyi et al. |
| 8,827,372 B2 * | 9/2014 | Yoon .................... B60N 2/5628 297/180.1 X |
| 8,958,955 B2 | 2/2015 | Hotary et al. |
| 8,971,839 B2 | 3/2015 | Hong |
| 8,979,191 B2 | 3/2015 | Friderich et al. |
| 8,989,697 B2 | 3/2015 | Leung et al. |
| 9,237,242 B2 | 1/2016 | Basir |
| 9,272,647 B2 | 3/2016 | Gawade et al. |
| 9,272,689 B2 | 3/2016 | Fung et al. |
| 9,277,385 B2 | 3/2016 | Iwamoto |
| 9,504,416 B2 | 11/2016 | Young et al. |
| 9,815,385 B2 | 11/2017 | Lippman et al. |
| 9,848,814 B2 | 12/2017 | Benson et al. |
| 9,883,821 B2 | 2/2018 | Muehlsteff |
| 9,978,283 B2 | 5/2018 | Jedrzejewski et al. |
| 9,980,680 B2 | 5/2018 | Matsumoto |
| 10,034,631 B1 | 7/2018 | Gallagher et al. |
| 10,210,409 B1 | 2/2019 | Migneco et al. |
| 10,213,147 B2 | 2/2019 | Gallagher et al. |
| 10,328,823 B2 | 6/2019 | O'Bannon et al. |
| 10,358,065 B2 | 7/2019 | McMillen et al. |
| 10,369,074 B2 | 8/2019 | Oberg et al. |
| 10,379,535 B2 | 8/2019 | Migneco et al. |
| 10,391,900 B2 | 8/2019 | Zhao et al. |
| 10,470,968 B2 | 11/2019 | Saren et al. |
| 10,471,868 B2 | 11/2019 | Wheeler |
| 10,492,979 B2 | 12/2019 | Norman et al. |
| 10,556,532 B2 | 2/2020 | Gallagher et al. |
| 10,569,668 B2 | 2/2020 | Migneco et al. |
| 10,576,855 B2 | 3/2020 | Dorfler et al. |
| 10,640,010 B2 | 5/2020 | Yetukuri et al. |
| 10,709,386 B2 | 7/2020 | Gallagher et al. |
| 10,807,439 B2 | 10/2020 | Migneco et al. |
| 10,898,708 B2 | 1/2021 | Franco-Obregon et al. |
| 2003/0039298 A1 * | 2/2003 | Eriksson ............... B60N 2/5635 374/109 |
| 2003/0075959 A1 | 4/2003 | Xue et al. |
| 2003/0209893 A1 * | 11/2003 | Breed .................. B60N 2/0248 280/735 |
| 2004/0119599 A1 | 6/2004 | Stevenson et al. |
| 2004/0129478 A1 * | 7/2004 | Breed .................. B60N 2/0276 180/273 |
| 2006/0244289 A1 * | 11/2006 | Bedro .................. B60N 2/5621 297/180.1 X |
| 2007/0118054 A1 | 5/2007 | Pinhas et al. |
| 2008/0161989 A1 * | 7/2008 | Breed ............... B60R 21/01532 701/31.4 |
| 2008/0216567 A1 * | 9/2008 | Breed ................... B60N 2/888 73/146.5 |
| 2008/0255731 A1 | 10/2008 | Mita et al. |
| 2008/0267460 A1 | 10/2008 | Aoki et al. |
| 2009/0008970 A1 | 1/2009 | Flory et al. |
| 2009/0030578 A1 | 1/2009 | Periot et al. |
| 2010/0087748 A1 | 4/2010 | Tobola et al. |
| 2011/0015468 A1 | 1/2011 | Aarts et al. |
| 2012/0080911 A1 | 4/2012 | Brykalski et al. |
| 2012/0086249 A1 | 4/2012 | Hotary et al. |
| 2012/0089299 A1 * | 4/2012 | Breed ................... B60N 2/888 701/36 |
| 2012/0116149 A1 | 5/2012 | Pilla et al. |
| 2013/0090816 A1 | 4/2013 | Huber |
| 2013/0127210 A1 * | 5/2013 | Jung .................... A47C 7/748 297/180.12 |
| 2013/0251216 A1 | 9/2013 | Smowton et al. |
| 2014/0070943 A1 | 3/2014 | Breed |
| 2014/0132042 A1 * | 5/2014 | Midderhoff ......... B60N 2/5685 297/180.12 |
| 2014/0207333 A1 | 7/2014 | Vandivier et al. |
| 2014/0319895 A1 | 10/2014 | Lange-Mao et al. |
| 2014/0361871 A1 | 12/2014 | Silva et al. |
| 2014/0375089 A1 * | 12/2014 | Qureshi ................ A47C 7/029 297/180.12 |
| 2015/0048658 A1 | 2/2015 | Gawade et al. |
| 2015/0084985 A1 | 3/2015 | Baudu |
| 2015/0126916 A1 | 5/2015 | Hall et al. |
| 2015/0266405 A1 | 9/2015 | Fitzpatrick et al. |
| 2015/0313475 A1 | 11/2015 | Benson et al. |
| 2015/0351692 A1 | 12/2015 | Pereny et al. |
| 2015/0352979 A1 | 12/2015 | O'Bannon et al. |
| 2015/0352990 A1 | 12/2015 | Zouzal et al. |
| 2015/0375653 A1 * | 12/2015 | Josefsson ............. B60R 16/037 219/202 |
| 2016/0001781 A1 | 1/2016 | Fung et al. |
| 2016/0003882 A1 | 1/2016 | Loftus |
| 2016/0143803 A1 | 5/2016 | Portales |
| 2016/0176409 A1 * | 6/2016 | Kirsch .................. A61M 21/02 701/37 |
| 2016/0250956 A1 | 9/2016 | Seiting et al. |
| 2016/0278709 A1 | 9/2016 | Ridao Granado et al. |
| 2017/0043681 A1 | 2/2017 | Seiller et al. |
| 2017/0086588 A1 | 3/2017 | Patrick et al. |
| 2017/0225591 A1 * | 8/2017 | Tobata ................. B60N 2/0244 |
| 2017/0274906 A1 | 9/2017 | Hassan et al. |
| 2017/0349061 A1 * | 12/2017 | Benson .................. B60N 2/914 |
| 2017/0361748 A1 | 12/2017 | Meachum et al. |
| 2018/0008507 A1 | 1/2018 | Saren et al. |
| 2018/0009343 A1 | 1/2018 | Saren et al. |
| 2018/0015853 A1 | 1/2018 | Lem et al. |
| 2018/0110960 A1 | 4/2018 | Youngblood et al. |
| 2018/0178692 A1 | 6/2018 | Zhao et al. |
| 2018/0215293 A1 * | 8/2018 | Gandhi ................... B60N 2/70 |
| 2018/0325264 A1 | 11/2018 | Gallagher et al. |
| 2018/0345833 A1 | 12/2018 | Gallagher et al. |
| 2018/0361897 A1 | 12/2018 | Lem et al. |
| 2019/0053761 A1 | 2/2019 | Young et al. |
| 2019/0054796 A1 | 2/2019 | Thomas |
| 2019/0126036 A1 | 5/2019 | Franco-Obregon et al. |
| 2019/0133511 A1 | 5/2019 | Migneco et al. |
| 2019/0168771 A1 | 6/2019 | Migneco et al. |
| 2019/0193591 A1 | 6/2019 | Migneco et al. |
| 2019/0239815 A1 | 8/2019 | Gallagher et al. |
| 2019/0275860 A1 | 9/2019 | Migneco et al. |
| 2019/0332902 A1 | 10/2019 | Gallagher et al. |
| 2019/0337431 A1 | 11/2019 | McMillen et al. |
| 2019/0344043 A1 | 11/2019 | Migneco et al. |
| 2020/0035237 A1 | 1/2020 | Kim et al. |
| 2020/0113344 A1 | 4/2020 | Youngblood et al. |
| 2020/0170576 A1 | 6/2020 | Lerner |
| 2020/0188211 A1 | 6/2020 | Ellermann |
| 2020/0231428 A1 | 7/2020 | Migneco et al. |

(56) References Cited

U.S. PATENT DOCUMENTS

| | | | |
|---|---|---|---|
| 2020/0238875 A1 | 7/2020 | Godlewski et al. | |
| 2020/0253381 A1 | 8/2020 | Dorfler et al. | |
| 2020/0324675 A1* | 10/2020 | Yamamoto | B60N 2/976 |
| 2021/0016686 A1* | 1/2021 | Yetukuri | B60N 2/002 |

FOREIGN PATENT DOCUMENTS

| | | |
|---|---|---|
| CN | 104252615 A | 12/2014 |
| CN | 205468657 U | 8/2016 |
| DE | 10027686 A1 | 1/2002 |
| DE | 10063478 A1 | 7/2002 |
| DE | 102004010626 A1 | 6/2005 |
| DE | 102004013674 A1 | 10/2005 |
| DE | 102006029871 A1 | 1/2008 |
| DE | 102008029339 A1 | 1/2009 |
| DE | 102009008421 A1 | 10/2009 |
| DE | 102009035566 A1 | 2/2010 |
| DE | 102009031331 A1 | 8/2010 |
| DE | 102009033041 A1 | 1/2011 |
| DE | 102010021332 A1 | 1/2011 |
| DE | 102010049152 A1 | 11/2011 |
| DE | 102011012431 A1 | 11/2011 |
| DE | 102011016073 A1 | 12/2011 |
| DE | 102011017238 A1 | 12/2011 |
| DE | 102011102021 A1 | 11/2012 |
| DE | 102011113100 A1 | 3/2013 |
| DE | 102011116194 A1 | 4/2013 |
| DE | 102012201430 A1 | 4/2013 |
| DE | 102012216869 A1 | 3/2014 |
| DE | 202015104103 U1 | 8/2015 |
| DE | 102014002942 A1 | 9/2015 |
| DE | 102015011460 A1 | 3/2016 |
| DE | 102015011461 A1 | 3/2016 |
| DE | 102017110812 A1 | 1/2018 |
| DE | 102016011481 A1 | 3/2018 |
| DE | 202017103162 U1 | 5/2018 |
| DE | 102018000765 A1 | 8/2019 |
| DE | 102018001230 A1 | 8/2019 |
| DE | 202019100400 U1 | 1/2020 |
| DE | 202019100710 U1 | 2/2020 |
| DE | 102018007921 A1 | 4/2020 |
| DE | 202019102879 U1 | 5/2020 |
| DE | 202019105369 U1 | 5/2020 |
| DE | 102019008724 A1 | 8/2020 |
| EP | 1077154 A2 | 2/2001 |
| EP | 1749477 A1 | 2/2007 |
| EP | 1932715 A1 | 6/2008 |
| EP | 2149475 A1 | 2/2010 |
| EP | 2205460 B1 | 3/2016 |
| FR | 2988654 A1 | 10/2013 |
| GB | 2512136 A | 9/2014 |
| JP | 2001269380 A | 10/2001 |
| JP | 2005137896 A | 6/2005 |
| JP | 2005237456 A | 9/2005 |
| JP | 2006014756 A | 1/2006 |
| JP | 3857869 B2 | 12/2006 |
| JP | 2009172145 A | 8/2009 |
| JP | 2012196253 A | 10/2012 |
| JP | 2013163405 A | 8/2013 |
| JP | 2019131049 A | 8/2019 |
| WO | 2012/039368 | 3/2012 |

OTHER PUBLICATIONS

Co-pending U.S. Appl. No. 15/930,777, filed May 13, 2020.
Co-pending U.S. Appl. No. 15/930,802, filed May 13, 2020.
Co-pending U.S. Appl. No. 15/930,835, filed May 13, 2020.
Co-pending U.S. Appl. No. 17/109,652, filed Dec. 2, 2020.

* cited by examiner

SEAT ASSEMBLY

TECHNICAL FIELD

The present disclosure generally relates to seat assemblies including seat assemblies that may be used in connection with reducing pain and discomfort associated with dysmenorrhea and/or sciatica.

BACKGROUND

This background description is set forth below for the purpose of providing context only. Therefore, any aspect of this background description, to the extent that it does not otherwise qualify as prior art, is neither expressly nor impliedly admitted as prior art against the instant disclosure.

Some seat assemblies may not be configured to reduce pain and/or discomfort associated with dysmenorrhea and/or sciatica. For example, some seat assemblies may not be configured to sense whether a user is experiencing pain and discomfort associated with dysmenorrhea or sciatica, and/or may not be configured to reduce said pain and discomfort.

There is a desire for solutions/options that minimize or eliminate one or more challenges or shortcomings of seat assemblies. The foregoing discussion is intended only to illustrate examples of the present field and is not a disavowal of scope.

SUMMARY

In embodiments, a seat assembly may include a seat having a seat base and a seat back, a temperature control unit disposed at least partially in the seat back, and/or an ECU connected with the temperature control unit. The ECU may be configured to receive an input related to (i) a first state corresponding to symptoms and/or discomfort associated with dysmenorrhea and/or (ii) a second state corresponding to symptoms and/or discomfort associated with sciatica. The ECU may be configured to operate the seat assembly according, at least in part, to the input (e.g., whether a user is in the first state and/or the second state).

With embodiments, a method of operating a seat assembly may include receiving information relating to whether a user is in (i) a first state corresponding to dysmenorrhea pain or discomfort, and/or (ii) a second state corresponding to sciatica pain or discomfort, activating a temperature control unit of the seat assembly to reduce pain or discomfort when said user is in at least one of the first state and the second state, and/or actuating a seat back of a seat of the seat assembly to reduce pain or discomfort when said user is in at least one of the first state and the second state.

The foregoing and other potential aspects, features, details, utilities, and/or advantages of examples/embodiments of the present disclosure will be apparent from reading the following description, and from reviewing the accompanying drawings.

BRIEF DESCRIPTION OF THE DRAWINGS

While the claims are not limited to a specific illustration, an appreciation of various aspects may be gained through a discussion of various examples. The drawings are not necessarily to scale, and certain features may be exaggerated or hidden to better illustrate and explain an innovative aspect of an example. Further, the exemplary illustrations described herein are not exhaustive or otherwise limiting, and are not restricted to the precise form and configuration shown in the drawings or disclosed in the following detailed description. Exemplary illustrations are described in detail by referring to the drawings as follows:

DETAILED DESCRIPTION

Reference will now be made in detail to embodiments of the present disclosure, examples of which are described herein and illustrated in the accompanying drawings. While the present disclosure will be described in conjunction with embodiments and/or examples, it will be understood that they do not limit the present disclosure to these embodiments and/or examples. On the contrary, the present disclosure covers alternatives, modifications, and equivalents.

Figure 1:
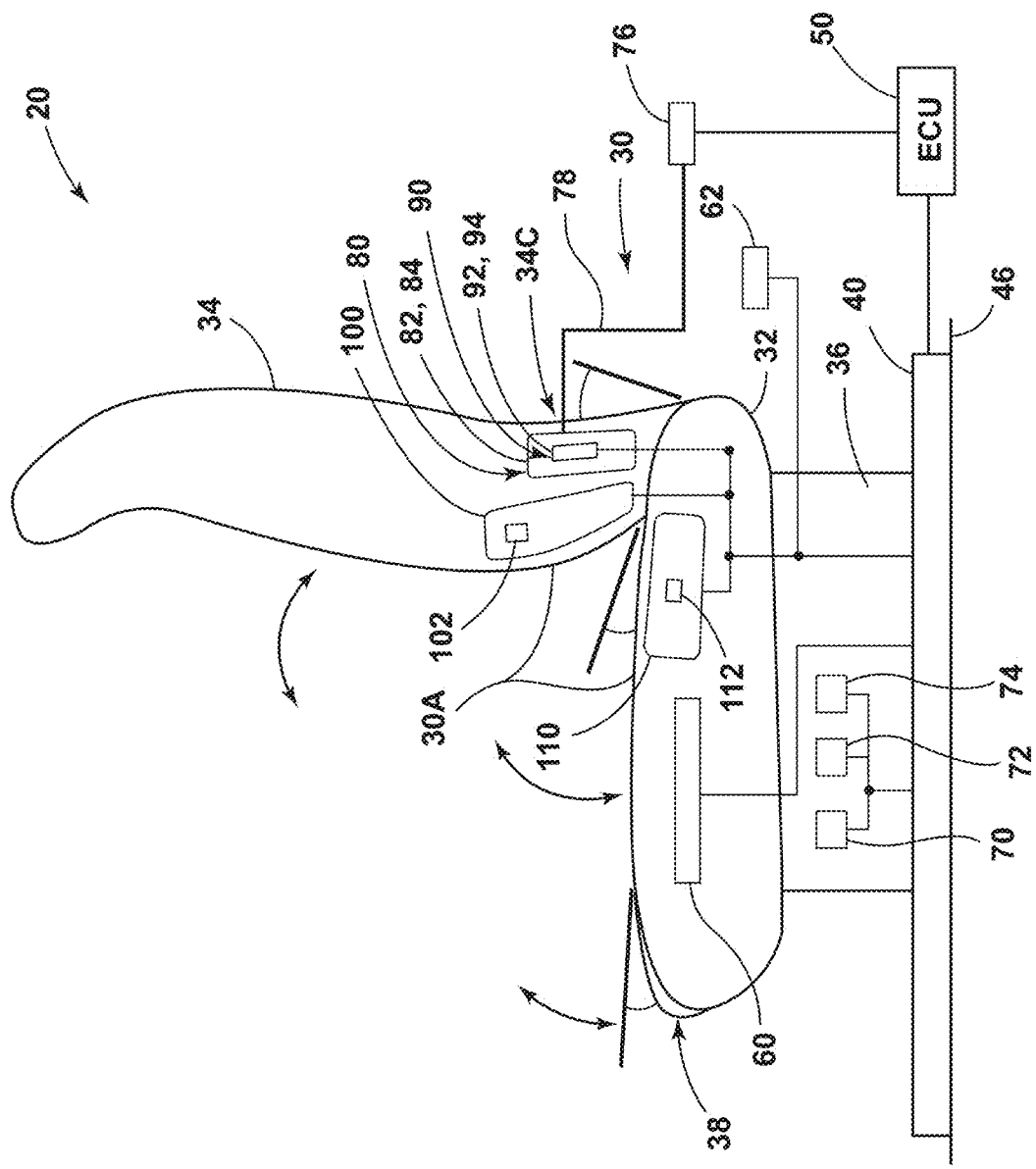
FIG. 1 is a side view generally illustrating an embodiment of a seat assembly according to teachings of the present disclosure.
Figure 2:
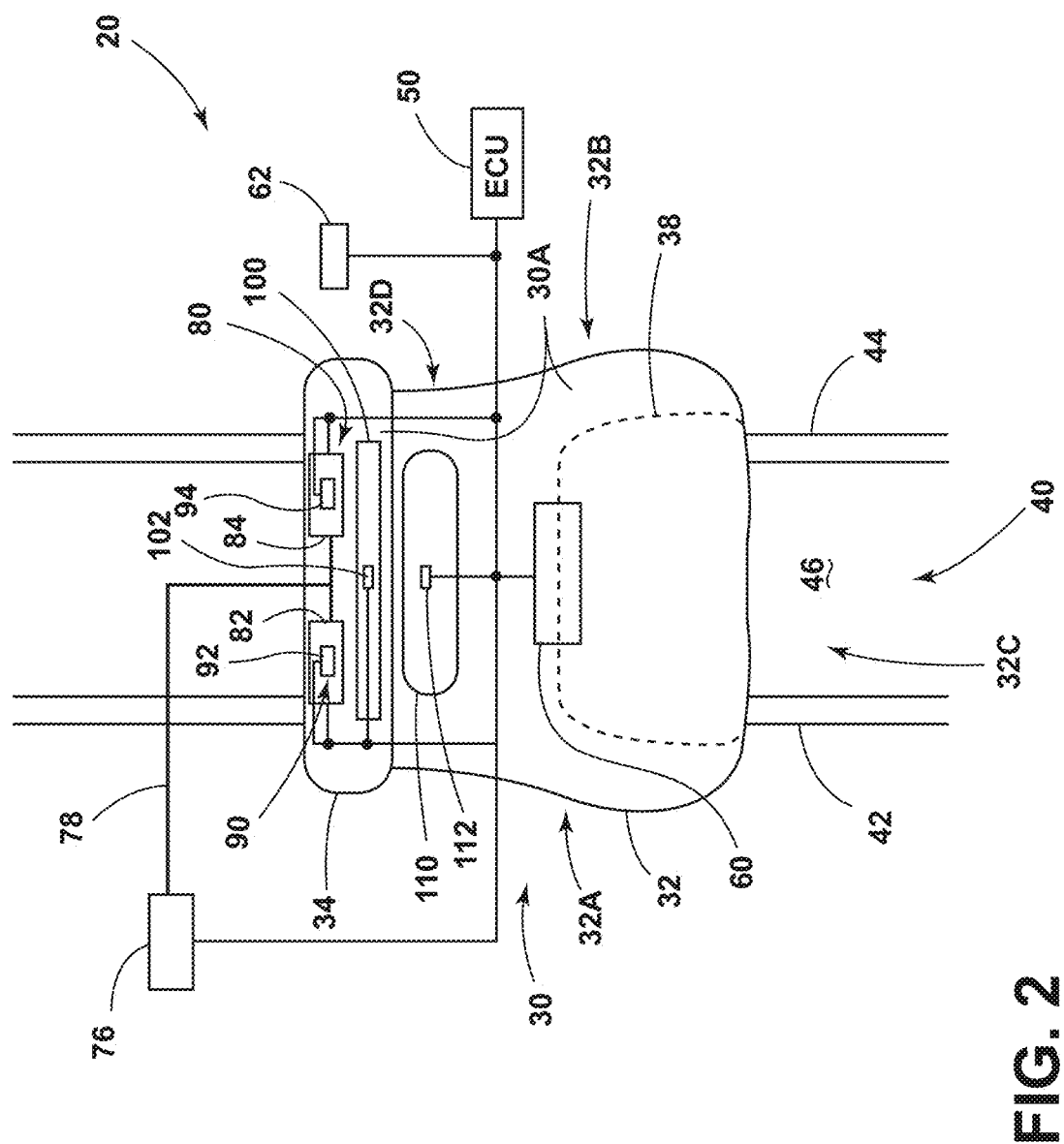
FIG. 2 is a top view generally illustrating an embodiment of a seat assembly according to teachings of the present disclosure.
Figure 3:
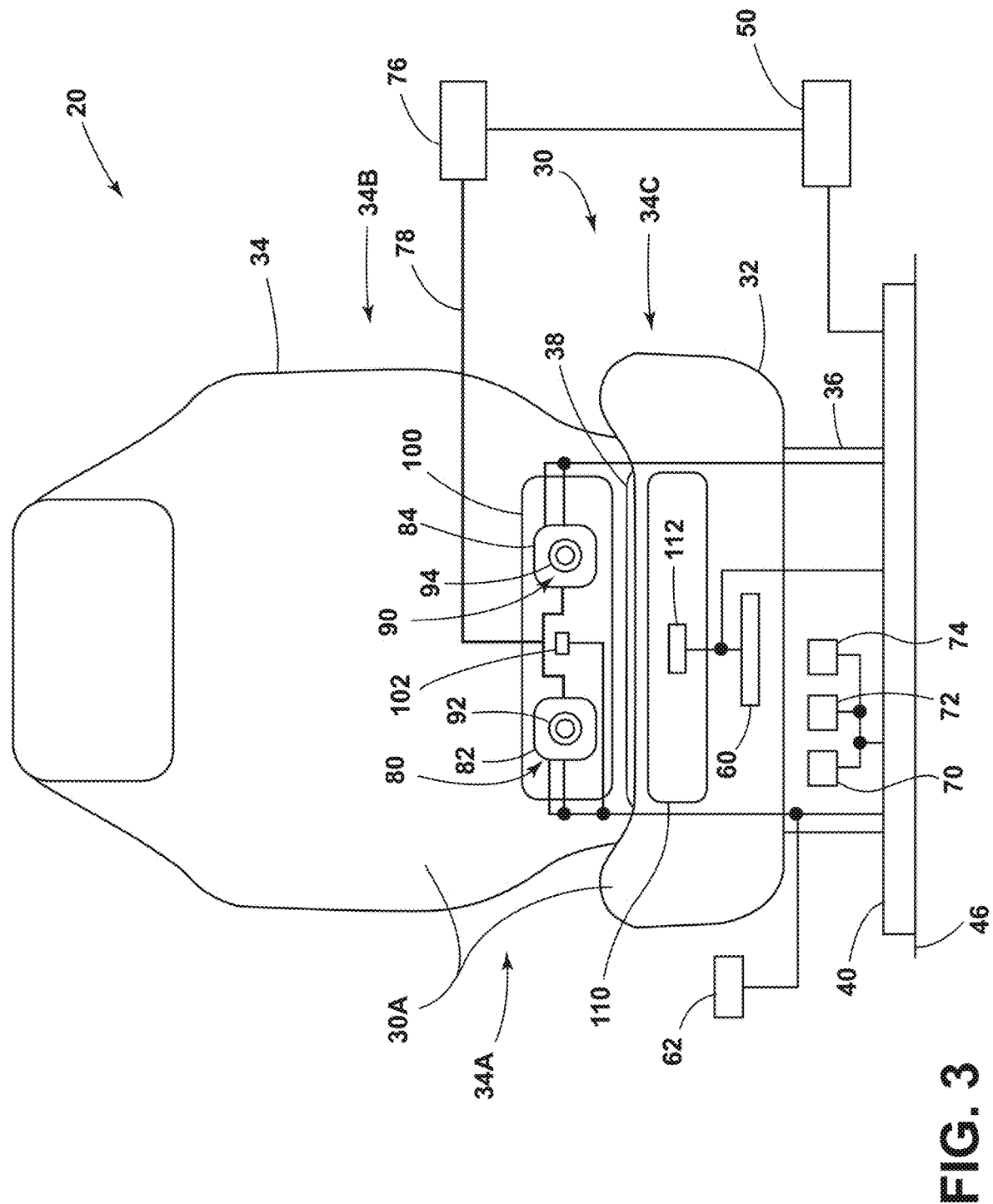
FIG. 3 is a front view generally illustrating portions of an embodiment of a seat assembly according to teachings of the present disclosure.
Figure 4:
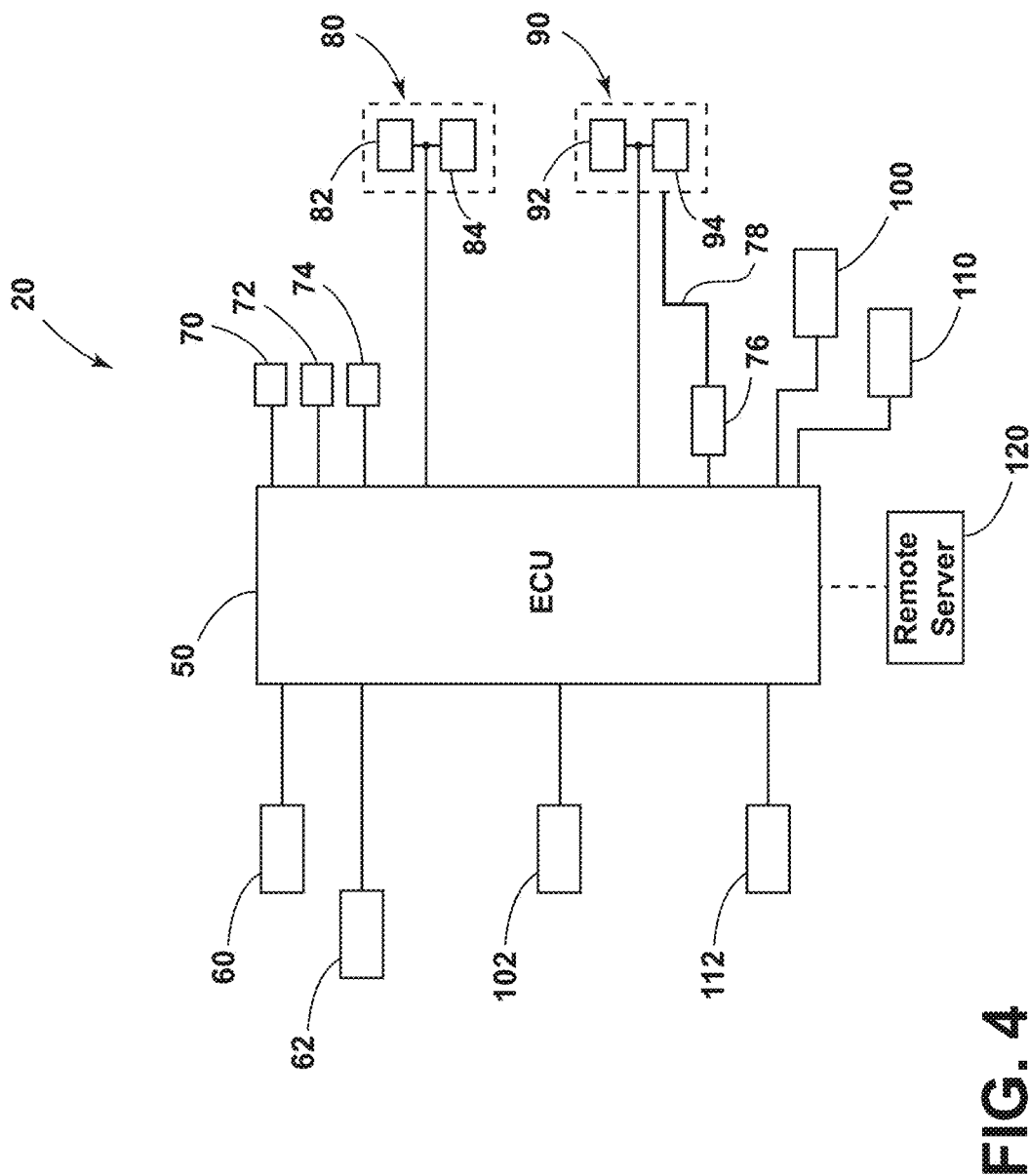
FIG. 4 is a schematic generally illustrating portions of an embodiment of a seat assembly according to teachings of the present disclosure.

In embodiments, such as generally illustrated in FIGS. 1, 2, and 3, the seat assembly 20 may include a seat 30, an electronic control unit (ECU) 50, and/or a sensor 60. The ECU 50 may be connected with the sensor 60, a first actuator 70, a second actuator 72, a third actuator 74, a bladder assembly 80, a pulsed electromagnetic field (PEMF) coil assembly 90, a first temperature control unit 100, and/or a second temperature control unit 110. The ECU 50 may be configured to control the first actuator 70, the second actuator 72, the third actuator 74, the bladder assembly 80, the PEMF coil assembly 90, the first temperature control unit 100, and/or the second temperature control unit 110, such as in response to information received by the ECU 50 and/or the sensor 60. For example and without limitation, the ECU 50 may activate and/or operate the first actuator 70, the second actuator 72, the third actuator 74, the bladder assembly 80, the PEMF coil assembly 90, the first temperature control unit 100, and/or the second temperature control unit 110 to reduce discomfort experienced/exhibited by a user of the seat 30 (e.g., a seat occupant). A temperature control unit 100, 110 may, for example and without limitation, include an air conditioner, a fan/air mover, and/or a heater, among other things.

In embodiments, such as generally illustrated in FIGS. 1, 2, and 3, the seat assembly 20 may include one or more seats 30. The seat 30 may include a seat base 32 and/or a seat back 34. The seat base 32 and/or the seat back 34 may be rotatably connected to each other and/or a support member 36 such that the seat base 32 and/or the seat back 34 may rotate to one or more of a variety of positions. The seat 30 may be selectively connected (e.g., electrically and/or mechanically) to a track assembly 40. The ECU 50 may be electrically connected to the seat 30, such as via the track assembly 40. The ECU 50 may be configured to at least partially control operation of the seat 30 (e.g., rotation of the seat base 32 and/or the seat back 34). The seat 30 may be connected (e.g., selectively) with the track assembly 40 via a support member 36. The support member 36 may be selectively connected with the track assembly 40. For example and without limitation, the support member 36 may be configured to be inserted vertically (e.g., in a Z-direction) and/or horizontally (e.g., in an X-direction or a Y-direction) into the track assembly 40. The seat 30 and/or the support member 36 may be configured to be removed vertically and/or horizontally from the track assembly 40, such as in a plurality of positions (e.g., two positions, three positions, or more positions) along the track assembly 40. The support member 36 may be configured to move along the track assembly 40 (e.g., in an X-direction and/or a Y-direction).

In embodiments, such as generally illustrated in FIG. 2, a track assembly 40 may include a first portion 42 and/or a second portion 44. The first portion 42 and/or the second portion 44 of the track assembly 40 may extend substantially in parallel (e.g., in the X-direction) and may be configured for connection with respective portions of the seat 30 and/or the support member 36. The track assembly 40 may be disposed on and/or fixed to a mounting surface 46 (e.g., a vehicle floor). The track assembly 40 may include one or more of a variety of shapes, sizes, and/or configurations. The track assembly 40 may extend in the X-direction and/or the Y-direction such that the seat 30 may move in the X-direction and/or the Y-direction along the track assembly 40.

With embodiments, such as generally illustrated in FIGS. 1, 2, 3, and 4, a seat assembly 20 may include a sensor 60. The sensor 60 may be configured to measure one or more of a variety of biomedical and/or biometric information of the user occupying the seat 30, and may be referred to herein as a biomedical sensor, but is not limited to a biomedical sensor. The sensor 60 may, for example and without limitation, be configured to identify a user, and/or sense (e.g., measure, detect, obtain, monitor, etc.) a heart rate, a breathing rate, a blood pressure, and/or other information related to the user. The sensor 60 may be disposed in the seat base 32 and/or the seat back 34, and/or may be disposed proximate the seat 30. The sensor 60 may be disposed proximate a seating surface 30A of the seat 30 such as to increase the accuracy of sensed biomedical information. The sensor 60 may be configured to sense if the user is exhibiting signs of discomfort. Additionally or alternatively, the seat assembly 20 may include a user interface 62 connected with the ECU 50. The user interface 62 may include an interactive display (e.g., touchscreen display) disposed proximate the seat 30 such that the user may interact with the user interface 62 when occupying the seat to manually control the seat assembly 20. The user interface 62 may be configured to receive one or more of a variety of inputs from the user (e.g., physical input, vocal input, gesture input, etc.). The user may manually activate the first actuator 70, the second actuator 72, the third actuator 74, the bladder assembly 80, the PEMF coil assembly 90, the first temperature control unit 100, and/or the second temperature control unit 110 via the user interface 62.

In embodiments, the ECU 50 may determine, via the sensor 60 and/or the user interface 62, that the user is in a first state (e.g., pain/discomfort associated with dysmenorrhea) and/or a second state (e.g., pain/discomfort associated with sciatica). The ECU 50 may be configured to automatically activate the first actuator 70, the second actuator 72, the third actuator 74, the bladder assembly 80, the PEMF coil assembly 90, the first temperature control unit 100, and/or the second temperature control unit 110 to reduce pain/discomfort when the user is in the first state and/or the second state.

With embodiments, a sensor 60 may, for example and without limitation, include portions of and/or be integrated at least partially with the bladder assembly 80. In some circumstances, the sensor 60 may include one or more pressure sensors connected to and/or integrated with the bladder assembly 80. Changes in pressure in the bladder assembly 80 may indicate that a user is fidgeting and/or is experiencing discomfort. The amount of a pressure change may correspond to the magnitude of the movement.

In embodiments, such as generally illustrated in FIGS. 1, 2, 3, and 4, a seat assembly 20 may include a first actuator 70 (e.g., a first electric motor) connected with the seat base 32, and/or a second actuator 72 (e.g., a second electric motor) connected with the seat back 34. The first actuator 70 and/or the second actuator 72 may be disposed at least partially in the seat 30 and/or the support member 36. The first actuator 70 may be configured to actuate (e.g., rotate) the seat base 32, and/or the second actuator 72 may be configured to actuate (e.g., rotate) the seat back 34. For example and without limitation, the first actuator 70 may be configured to rotate the seat base 32 in a first direction (e.g., clockwise in FIG. 1) and/or a second direction (e.g., counterclockwise in FIG. 2). The first actuator 70 may, for example, rotate the seat base 32 about 90 degrees or more or less. The second actuator 72 may be configured to rotate the seat back 34 in a first direction (e.g., clockwise in FIG. 1) and/or a second direction (e.g., counterclockwise in FIG. 2). The second actuator 72 may, for example, rotate the seat back 34 about 180 degrees or more or less. The first actuator 70 and/or the second actuator 72 may be electrically connected (e.g., via wired and/or wireless connection) with the ECU 50. The ECU 50 may be configured to control the first actuator 70 and/or the second actuator 72. The first actuator 70 and/or the second actuator 72 may be manually controlled by the user via the user interface 62 and/or may be automatically controlled by the ECU 50 (e.g., when automatically reducing pain/discomfort).

In embodiments, such as generally illustrated in FIGS. 1, 2, and 3, the seat assembly 20 may include a leg support portion 38. The leg support portion 38 may be connected and/or at least partially integrated with the seat base 32. The leg support portion 38 may be disposed proximate a front side 32C of the seat base 32 (see, e.g., FIG. 2). The leg support portion 38 may include one or more of a variety of shapes, sizes, and/or configurations. For example and without limitation, the leg support portion 38 may be substantially rectangular-shaped, curved, and/or planar. The leg support portion 38 may be configured to move separately/independently from and/or with the seat base 32. The leg support portion 38 may be configured to provide additional position adjustment for the user, such as adjustment of the position of the knees/legs of the user. For example and without limitation, the seat base 32 may be actuated to a desired position and the leg support portion 38 may also be actuated to provide additional support positions (e.g., inclined positions) for the knees of the user, such as to reduce pain/discomfort associated with sciatica.

With embodiments, the leg support portion 38 may be connected with a third actuator 74 (e.g. a third electrical motor). The third actuator 74 may be configured to actuate the leg support portion 38. The third actuator 74 may be electrically connected (e.g., wired and/or wirelessly) with the ECU 50. The ECU 50 control the third actuator 74 to move (e.g., shift, rotate, tilt, etc.) the leg support portion 38 in a first direction (e.g., clockwise in FIG. 2) and/or a second direction (e.g., counterclockwise in FIG. 2). The third actuator 74 may, for example, rotate the leg support portion 38 about 30 degrees or more or less. The ECU 50 may be configured to automatically control operation and/or rotation of the third actuator 74, such as to reduce pain and/or discomfort of the user. Additionally or alternatively, the user may control operation and/or rotation of the third actuator 74 via the user interface 62.

With embodiments, such as generally illustrated in FIGS. 1, 2, 3, and 4, the seat assembly may include a bladder assembly 80. The bladder assembly 80 may include any number of bladders 82, 84 disposed in the seat base 32 and/or the seat back 34. For example and without limitation, the bladder assembly 80 may include a first bladder 82 and/or a second bladder 84. The first bladder 82 and/or the second bladder 84 may be disposed substantially in the seat back 34. The first bladder 82 and/or the second bladder 84 may be disposed proximate a lower portion 34C of the seat back 34. The first bladder 82 may be disposed proximate a first side 34A of the seat back 34, and/or the second bladder 84 may be disposed proximate a second side 34B of the seat back 34. The first side 34A of the seat back 34 may be opposite the second side 34B of the seat back 34.

In embodiments, the bladder assembly 80 may be electrically connected (wired and/or wirelessly) with the ECU 50 such that the ECU 50 may control the bladder assembly 80. For example and without limitation, the ECU 50 may be configured to independently control operation of the first bladder 82 and/or the second bladder 84. The ECU 50 may be configured to inflate and/or deflate the bladders 82, 84 of the bladder assembly 80. The ECU 50 may be configured to inflate and/or deflate the bladders 82, 84 such as to adjust a position of the user and/or massage the user while occupying the seat 30. Inflating and deflating the bladders 82, 84 (e.g., adjusting a position of the user and/or massaging the user) may reduce pain/discomfort associated with the user in the first state and/or the second state. For example and without limitation, if the ECU 50 senses, via the sensor 60, that the user is in the first state and/or the second state, the ECU 50 may automatically activate the bladder assembly 80 to reduce pain/discomfort accordingly. Additionally or alternatively, the user may manually activate the first bladder 82 and/or the second bladder 84 of the bladder assembly 80 via the user interface 62. The user interface 62 may be configured to control a level of inflation for the first bladder 82 and/or the second bladder 84 when manually adjusting the position of the user. The user interface 62 may be configured to control an intensity level for the first bladder 82 and/or the second bladder 84 such as when manually activated by the user to massage.

With embodiments, the ECU 50 may be configured control operation (e.g., inflation/deflation) of the bladder assembly 80 via a fluid source 76 that may be in fluid communication with the bladder assembly 80, such as via one or more fluid conduits 78 (e.g., tubes, hoses, ducts, etc.). The fluid source 76 may, for example and without limitation, include a fluid pump, a fan, fluid reservoir, and/or one or more control valves, among other components, that may be configured to selectively provide fluid (e.g., air) to and/or remove fluid from the bladder assembly 80.

In embodiments, such as generally illustrated in FIGS. 1, 2, 3, and 4, a seat assembly 20 may include a pulsed electromagnetic field (PEMF) coil assembly 90. The PEMF coil assembly 90 may include one or more PEMF coils 92, 94. For example and without limitation, the PEMF coil assembly 90 may include a first coil 92 and/or a second coil 94. The first coil 92 may be disposed proximate the first side 34A of the seat back 34, and/or the second coil 94 may be disposed proximate the second side 34B of the seat back 34. The coils 92, 94 may, for example and without limitation, be disposed at least partially within the bladder assembly 80. In some circumstances, the first coil 92 may be disposed at least partially within the first bladder 82, and/or the second coil 94 may be disposed at least partially within the second bladder 84. The PEMF coil assembly 90 may be electrically connected (e.g., via wired and/or wireless connection) with the ECU 50, and/or the ECU 50 may activate and/or deactivate the PEMF coil assembly 90.

With embodiments, activating the PEMF coil assembly 90 may reduce pain/discomfort associated with osteo-articular pain and/or inflammation. Additionally or alternatively, activating the PEMF coil assembly 90 may reduce pain/discomfort associated with dysmenorrhea (e.g., when the user is in the first state) and/or sciatica (e.g., when the user is in the second state). The PEMF coil assembly 90 may be disposed proximate a lumbar area and/or a sacral area of the user (e.g., proximate a lower portion 34C of the seat back 34). For example and without limitation, the ECU 50 may control the PEMF coil assembly 90 to apply PEMF-based therapy to the lumbo-sacral-area of the user when the user is in the first state and/or the second state. The ECU 50 may be configured to automatically activate the PEMF coil assembly 90 upon determining/sensing that the user is in the first state and/or the second state. Additionally or alternatively, the user may manually activate the first coil 92 and/or the second coil 94 of the PEMF assembly 90, such as via a user interface 62 that may be connected with the ECU 50 and/or the PEMF coil assembly 90.

In embodiments, such as generally illustrated in FIGS. 1, 2, 3, and 4, the seat assembly 20 may include a first temperature control unit 100. The first temperature control unit 100 may be disposed at least partially in and/or aligned with a lower portion 34C of the seat back 34 (e.g., such as to be generally aligned with a lumbar and/or sacral areas of the user). The first temperature control unit 100 may be disposed proximate a seating surface 30A of the seat back 34 such that the user may sense a temperature of the first temperature control unit 100. The first temperature control unit 100 may be electrically connected (e.g., via wired and/or wireless connection) with the ECU 50, and/or the ECU 50 may control operation of the first temperature control unit 100. The first temperature control unit 100 may be configured to provide high-intensity heat, such as proximate the lumbo-sacral area of the user. High intensity heat may, for example and without limitation, include temperatures (e.g., temperatures at a seating surface 30A) of about 37 degrees Celsius to about 43 degrees Celsius at the skin level of the user or more or less, which may be higher than temperatures provided by temperature control units of other types of seat assemblies (e.g., seat assemblies not configured for reducing pain/discomfort associated with dysmenorrhea). The ECU 50 may be configured to automatically activate the first temperature control unit 100 (e.g. to apply high-intensity heat) if the user is in the first state (e.g., the user is experiencing pain/discomfort due to dysmenorrhea).

With embodiments, such as generally illustrated in FIGS. 1, 2, 3, and 4, a seat assembly 20 may include a first temperature sensor 102. The first temperature sensor 102 may be disposed proximate a seating surface 30A of the seat 30, such as at or about the lower portion 34C of the seat back 34. The first temperature sensor 102 may be electrically connected (e.g., via wired and/or wireless connection) with the ECU 50. The ECU 50 may sense a seat surface temperature via the first temperature sensor 102, such as to verify that the first temperature control unit 100 is operating at or below a threshold temperature. If the seat surface temperature is greater than the threshold temperature (e.g., a temperature greater than 43 degrees Celsius), the ECU 50 may deactivate and/or reduce the temperature of the first temperature control unit 100, such as to avoid injury to the user.

In embodiments, such as generally illustrated in FIGS. 1, 2, 3, and 4, a seat assembly 20 may include a second temperature control unit 110. The second temperature control unit 110 may be proximate a seating surface 30A of the seat 30, such as of the seat base 32, which may facilitate the user feeling the effects (e.g., heating, cooling, etc.) of the second temperature control unit 110. The second temperature control unit 110 may be electrically connected (e.g., via wired and/or wireless connection) with the ECU 50, and/or the ECU 50 may control operation of the second temperature control unit 110, such as according, at least in part, to temperature information from a second temperature sensor 112 that may be disposed proximate the second temperature control unit 110 and/or the seat base 32. The ECU 50 may be configured to control the second temperature control unit 110 to provide heat and/or cooling. The ECU 50 may be configured to automatically raise and/or lower the temperature of the second temperature control unit 110 (e.g., according to settings associated with a specific user). Additionally or alternatively, a user may manually raise and/or lower the temperature of the temperature control unit 110, such as via the user interface 62. The second temperature control unit 110 may not be configured to reach a temperature greater than about 37 degrees Celsius at the skin level of the user (e.g., may not be configured to apply high intensity heat). The ECU 50 may raise and/or lower the temperature of the second temperature control unit 110 to reduce pain/discomfort when the user is in the first state and/or the second state.

With embodiments, the ECU 50 may be configured to receive information (e.g., via sensors, manual input, and/or remotely) indicating that the user is in the first state (e.g., experiencing pain/discomfort due to dysmenorrhea). The ECU 50 may receive input from the user via the user interface 62 informing the ECU that the user is in the first state. Additionally or alternatively, the ECU 50 may be connected with a remote server 120 that may be configured to receive information indicating if a user is likely to experience and/or is experiencing pain/discomfort associated with dysmenorrhea (see, e.g., FIG. 4). The remote server 120 may be configured for connection with one or more devices (e.g., computers, tablets, smartphones, etc.) and/or applications (e.g., internet applications, smartphone applications) associated with the user that may facilitate predicting and/or determining that the user is in the first state. For example and without limitation, a remote server 120 may include information obtained via a smartphone application that tracks a menstrual cycle of the user, and the user may grant the ECU 50 to access that information. The ECU 50 may then utilize that information to predict when a user is likely to be in the first state. With embodiments, the ECU 50 may be configured for machine learning to predict when the user may activate one or more functions of the seat assembly 20 based upon a recorded/monitored history of use of the functions by the user.

Figure 5:
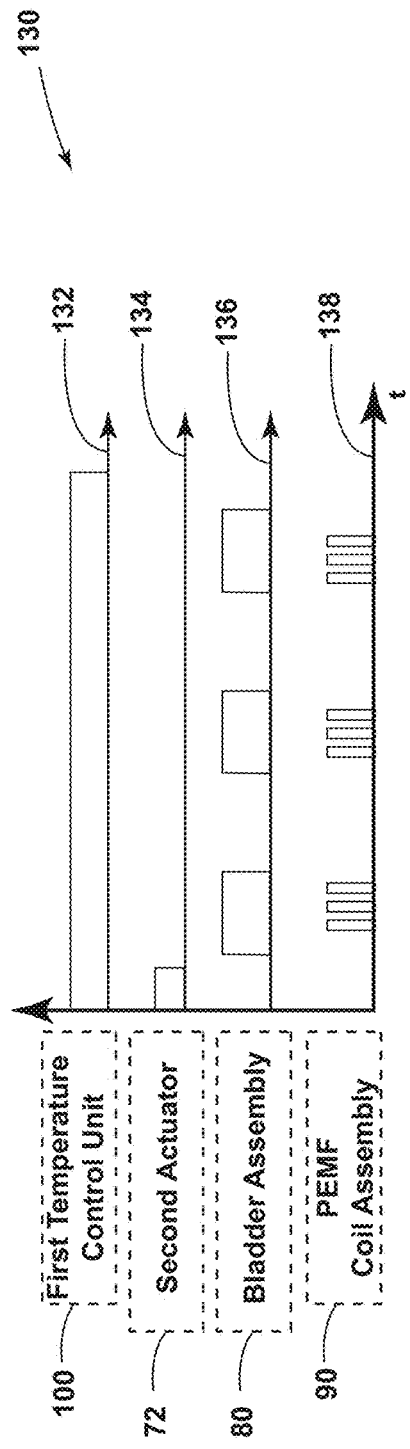
FIG. 5 is a graph generally illustrating an activation of portions of an embodiment of a seat assembly according to teachings of the present disclosure.

In embodiments, such as generally illustrated in FIG. 5, the ECU 50 may automatically activate the seat assembly 20 upon determining that the user is in the first state (e.g., see activation graph 130 of FIG. 5). As generally shown by plot 132, the ECU 50 may automatically activate the first temperature control unit 100, such as to apply high intensity heat to the lower portion 34C of the seat back 34 (e.g., the lumbar area of the user). While the first temperature control unit 100 is activated by the ECU 50, the ECU 50 may automatically activate the first actuator 70 and/or the second actuator 72. For example, the ECU 50 may control the second actuator 72 to rotate/recline the seat back 34 (e.g., about 1 degree to about 5 degrees) to reduce pain/discomfort when the user is in the first state (see, e.g., plot 134) and/or may maintain the position of the seat base 32.

With embodiments, the ECU 50 may automatically activate the bladder assembly 80 and/or the PEMF coil assembly 90 to reduce user discomfort when the user is in the first state (see, e.g., plots 136, 138), which may include activating the bladder assembly 80 and/or the PEMF coil assembly 90 while the first temperature control unit 100 is activated and/or the seat back 34 is reclined. When activating the bladder assembly 80, the ECU 50 may inflate and/or deflate the first bladder 82 and/or the second bladder 84 to provide acupressure therapy to the lumbar area of the user. The ECU 50 may receive input from the user via the user interface 62 corresponding to a desired frequency and/or intensity level of the bladders 82, 84 when applying acupressure and/or massage therapy. The user may adjust operation of the first bladder 82 and/or the second bladder 84 to a preferred configuration, such as to minimize discomfort for the specific user. The ECU 50 may cyclically/repeatedly inflate and/or deflate the first bladder 82 and/or the second bladder 84 to provide a massaging effect. The ECU 50 may automatically activate the PEMF coil assembly 90, such as while the bladder assembly 80 is activated. Activating the PEMF coil assembly 90 may include activating the first coil 92 and/or the second coil 94 to provide PEMF therapy to the user. The ECU 50 may be configured to cyclically apply PEMF therapy to the user. The ECU 50 may, for example and without limitation, provide PEMF therapy while the first bladder 82 and/or the second bladder 84 are inflated to reduce pain/discomfort associated with dysmenorrhea.

Figure 6:
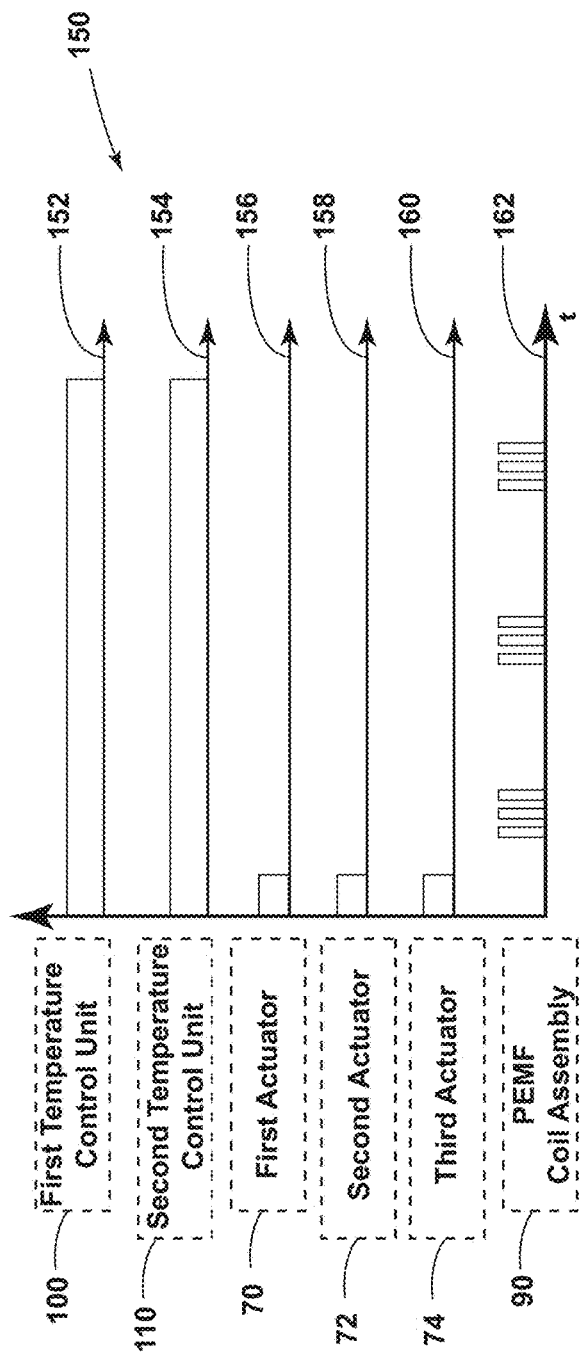
FIG. 6 is a graph generally illustrating an activation of portions of an embodiment of a seat assembly according to teachings of the present disclosure.

With embodiments, the ECU 50 may be configured to receive information, such as from the user interface 62, indicating that the user is in the second state (e.g., experiencing pain/discomfort due to sciatica). The ECU 50 may activate functions of the seat assembly 20 (e.g., automatically) in one or more of a variety of manners to reduce pain/discomfort associated with sciatica (e.g., see activation graph 150 of FIG. 6). For example and without limitation, the ECU 50 may activate the first temperature control unit 100 and/or the second temperature control unit 110, such as to provide heat or cooling to one or more portions of the body of the user. The user interface 62 may receive (e.g., directly from the user occupying the seat 30 via the user interface 62) a preferred temperature for the first temperature control unit 100 and/or the second temperature control unit 110, and the ECU 50 may activate the temperature control units 100, 110 at the preferred temperatures to reduce pain/discomfort associated with sciatica (see, e.g., plots 152, 154). While the first temperature control unit 100 and/or the second temperature control unit 110 are activated, the ECU 50 may adjust a position of the seat 30.

In embodiments, the ECU 50 may adjust a position of the seat 30 and/or the user to reduce pain/discomfort associated with sciatica. For example and without limitation, the user may provide information, such as a preferred seat position (e.g., a discomfort reduction position), to the ECU 50 for limiting and/or reducing pain associated with sciatic. Additionally or alternatively, the user may provide a memory position for the seat 30 for situations in which the user is not in the first state and/or is not in the second state. The user may provide a preferred position of the seat base 32, the seat back 34, and/or the leg support portion 38 via the user interface 62. The ECU 50 may store the preferred position, and/or the ECU 50 may move the seat 30, via one or more of the first, second, and third actuators 70, 72, 74 (see, e.g., plots 156, 158, 160) into the preferred seat position upon sensing and/or receiving input that the user is in the second state. For example and without limitation, the ECU 50 may control the first actuator 70 to rotate the seat base 32 about 1 degree to about 5 degrees, the ECU 50 may control the second actuator 72 to rotate the seat back 34 about 1 degree to about 5 degrees, and/or the ECU 50 may be configured to control the third actuator 74 to rotate the leg support portion 38 about 1 degree to about 5 degrees or more or less, to reduce pain/discomfort associated with sciatica and/or to reduce compression of the sciatic nerve of the user. In some circumstances, the preferred position may involve moving the back of the user to a more vertical position and/or lifting the knees/legs of the user, at least to some degree, which may correspond to an anti-Lasegue maneuver. The user may provide the preferred position (e.g., a preferred anti-Lasegue position), the ECU 50 may determine a preferred position, and/or the ECU 50 may receive the preferred position from the remote server 120. The ECU 50 may store the preferred position and may automatically move the seat 30 to the preferred position, such as if the user indicates (e.g., via the user interface 62) that the user is experiencing pain associated with sciatica.

In embodiments, the ECU 50 may be configured to control the bladder assembly 80 to shift the position of the user, such as if movement of the seat 30 is restricted (e.g., if movement would contact another seat, another user, or other component). For example and without limitation, the ECU 50 may inflate the bladder assembly 80 proximate the knees or legs of a user to raise the knees or legs of the user to reduce pain associated with sciatica.

In embodiments, the ECU 50 may activate the PEMF coil assembly 90 to reduce pain associated with sciatica (see, e.g., plot 162), such as while the temperature control units 100, 110 are activated and/or the seat 30 is in or moving to a preferred position. The ECU 50 may activate the first coil 92 and/or the second coil 94 of the PEMF coil assembly 90 to provide PEMF therapy to the user. The ECU 50 may be configured to cyclically apply PEMF therapy to the user to reduce pain/discomfort associated with sciatica.

Figure 7:
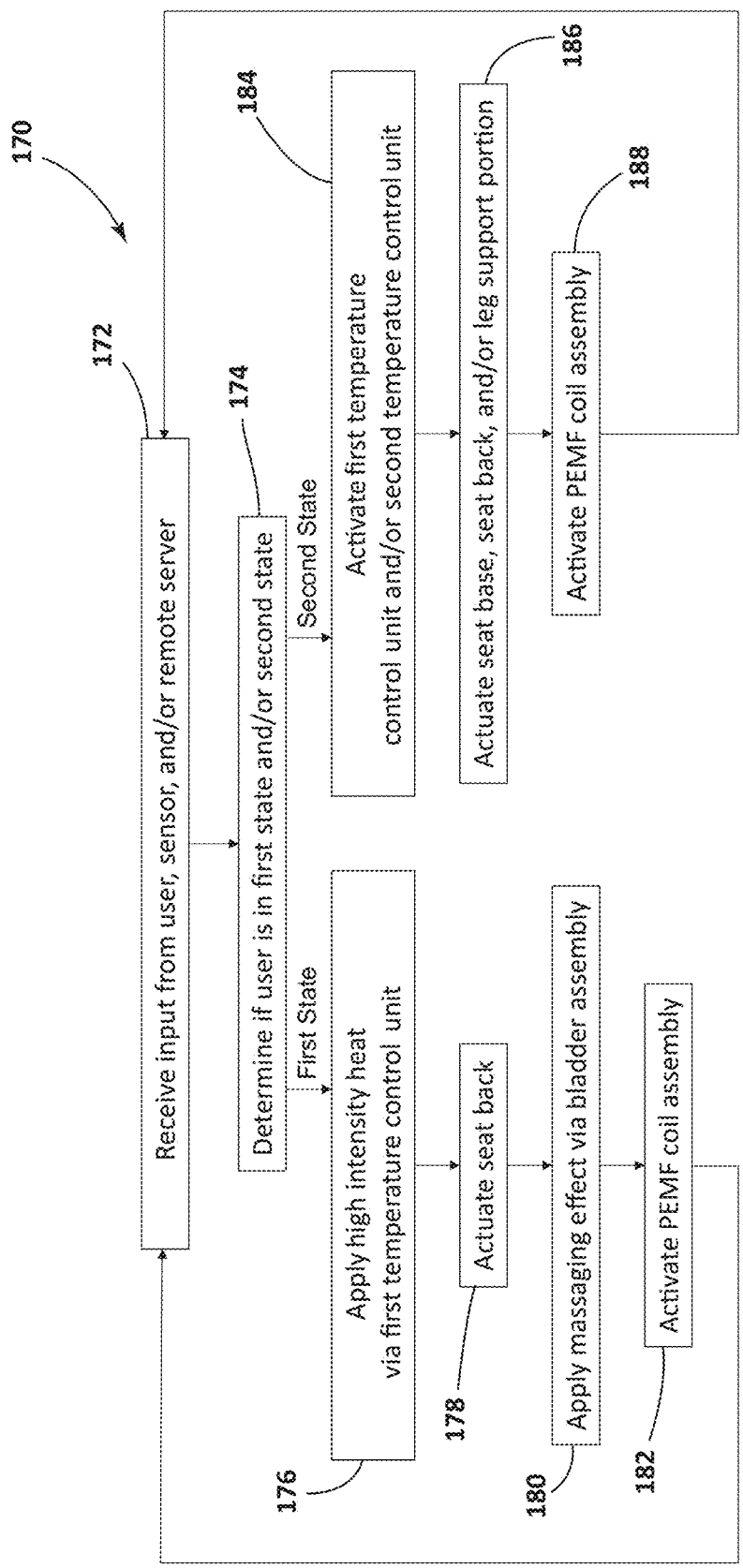
FIG. 7 is a flow chart generally illustrating a method of operating an embodiment of a seat assembly according to teachings of the present disclosure.

With embodiments, such as generally illustrated in FIG. 7, a method 170 of operating a seat assembly 20 may include the ECU 50 receiving information from the sensor 60, the user (via the user interface 62), and/or the remote server 120 relating to whether a user is in a first state (e.g., experiencing pain/discomfort due to dysmenorrhea) and/or a second state (e.g., experiencing pain/discomfort associated with sciatica) (step 172). The ECU 50 may be configured to utilize the information and determine the state of the user (step 174). In some instances, the user may be in the first state and the second state at the same time.

In embodiments, if the user is in the first state, the method 170 may include providing high intensity heating to the user via the first temperature control unit 100 (step 176). The method 170 may include actuating the seat back 34 via the second actuator (step 178). The ECU 50 may apply a massaging effect via the bladder assembly 80 (step 180) and/or the ECU 50 may activate the PEMF coil assembly 90 to reduce pain/discomfort due to dysmenorrhea (step 182).

With embodiments, if the user is in the second state, the method 170 may include activating the first temperature control unit 100 and/or the second temperature control unit 110, such as according to temperature preferences of the user (step 184). The method 170 may include actuating the seat base 32, the seat back 34, and/or the leg support portion 38 such that the seat 30 may be disposed in a user preferred position to reduce pain/discomfort associated with sciatica (step 186). The method 170 may include activating the PEMF coil assembly 90 to reduce pain/discomfort associated with sciatica (step 188).

In examples, an ECU (e.g., ECU 50) may include an electronic controller and/or include an electronic processor, such as a programmable microprocessor and/or microcontroller. In embodiments, an ECU may include, for example, an application specific integrated circuit (ASIC). An ECU may include a central processing unit (CPU), a memory (e.g., a non-transitory computer-readable storage medium), and/or an input/output (I/O) interface. An ECU may be configured to perform various functions, including those described in greater detail herein, with appropriate programming instructions and/or code embodied in software, hardware, and/or other medium. In embodiments, an ECU may include a plurality of controllers. In embodiments, an ECU may be connected to a display (e.g., a user interface 62), such as a touchscreen display.

Various examples/embodiments are described herein for various apparatuses, systems, and/or methods. Numerous specific details are set forth to provide a thorough understanding of the overall structure, function, manufacture, and use of the examples/embodiments as described in the specification and illustrated in the accompanying drawings. It will be understood by those skilled in the art, however, that the examples/embodiments may be practiced without such specific details. In other instances, well-known operations, components, and elements have not been described in detail so as not to obscure the examples/embodiments described in the specification. Those of ordinary skill in the art will understand that the examples/embodiments described and illustrated herein are non-limiting examples, and thus it can be appreciated that the specific structural and functional details disclosed herein may be representative and do not necessarily limit the scope of the embodiments.

Reference throughout the specification to "examples, "in examples," "with examples," "various embodiments," "with embodiments," "in embodiments," or "an embodiment," or the like, means that a particular feature, structure, or characteristic described in connection with the example/embodiment is included in at least one embodiment. Thus, appearances of the phrases "examples, "in examples," "with examples," "in various embodiments," "with embodiments," "in embodiments," or "an embodiment," or the like, in places throughout the specification are not necessarily all referring to the same embodiment. Furthermore, the particular features, structures, or characteristics may be combined in any suitable manner in one or more examples/embodiments. Thus, the particular features, structures, or characteristics illustrated or described in connection with one embodiment/example may be combined, in whole or in part, with the features, structures, functions, and/or characteristics of one or more other embodiments/examples without limitation given that such combination is not illogical or non-functional. Moreover, many modifications may be made to adapt a particular situation or material to the teachings of the present disclosure without departing from the scope thereof.

It should be understood that references to a single element are not necessarily so limited and may include one or more of such element. Any directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of examples/embodiments.

Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. The use of "e.g." in the specification is to be construed broadly and is used to provide non-limiting examples of embodiments of the disclosure, and the disclosure is not limited to such examples. Uses of "and" and "or" are to be construed broadly (e.g., to be treated as "and/or"). For example and without limitation, uses of "and" do not necessarily require all elements or features listed, and uses of "or" are inclusive unless such a construction would be illogical.

While processes, systems, and methods may be described herein in connection with one or more steps in a particular sequence, it should be understood that such methods may be practiced with the steps in a different order, with certain steps performed simultaneously, with additional steps, and/or with certain described steps omitted.

All matter contained in the above description or shown in the accompanying drawings shall be interpreted as illustrative only and not limiting. Changes in detail or structure may be made without departing from the present disclosure.

It should be understood that an electronic control unit (ECU), a system, and/or a processor as described herein may include a conventional processing apparatus known in the art, which may be capable of executing preprogrammed instructions stored in an associated memory, all performing in accordance with the functionality described herein. To the extent that the methods described herein are embodied in software, the resulting software can be stored in an associated memory and can also constitute means for performing such methods. Such a system or processor may further be of the type having ROM, RAM, RAM and ROM, and/or a combination of non-volatile and volatile memory so that any software may be stored and yet allow storage and processing of dynamically produced data and/or signals.

It should be further understood that an article of manufacture in accordance with this disclosure may include a non-transitory computer-readable storage medium having a computer program encoded thereon for implementing logic and other functionality described herein. The computer program may include code to perform one or more of the methods disclosed herein. Such embodiments may be configured to execute via one or more processors, such as multiple processors that are integrated into a single system or are distributed over and connected together through a communications network, and the communications network may be wired and/or wireless. Code for implementing one or more of the features described in connection with one or more embodiments may, when executed by a processor, cause a plurality of transistors to change from a first state to a second state. A specific pattern of change (e.g., which transistors change state and which transistors do not), may be dictated, at least partially, by the logic and/or code.

What is claimed is:

1. A seat assembly, including:
   a seat having a seat base and a seat back;
   a temperature control unit disposed at least partially in the seat back; and
   an electronic control unit (ECU) connected with the temperature control unit;
   wherein the ECU is configured to receive an input related to (i) a first state corresponding to symptoms and/or discomfort associated with dysmenorrhea and/or (ii) a second state corresponding to symptoms and/or discomfort associated with sciatica; and
   the ECU is configured to operate the seat assembly according, at least in part, to the input.

2. The seat assembly of claim 1, wherein the ECU is configured to operate the temperature control unit at a temperature of at least about 37 degrees Celsius at a skin level.

3. The seat assembly of claim 1, wherein the ECU is configured to operate the temperature control unit at a temperature range from about 37 degrees Celsius to about 43 degrees Celsius at a skin level.

4. The seat assembly of claim 1, wherein in the first state, the ECU is configured to automatically activate an actuator to recline the seat back.

5. The seat assembly of claim 1, including a bladder assembly disposed substantially in the seat back; and
   wherein the ECU is configured to automatically provide a massaging effect to reduce discomfort via the bladder assembly when in the first state.

6. The seat assembly of claim 1, including a pulsed electromagnetic field (PEMF) coil assembly disposed at least partially in the seat back;
   wherein the ECU is configured to automatically activate the PEMF coil assembly to reduce discomfort when in at least one of the first state and the second state; and
   wherein the PEMF coil assembly is configured to provide PEMF therapy proximate a lumbar area and/or a sacral area of a user.

7. The seat assembly of claim 1, wherein the ECU is connected with a remote server configured to provide the input; and
   the input includes user information associated with the first state and/or the second state.

8. The seat assembly of claim 7, wherein the user information associated with the first state and/or the second state includes at least one of a user's (i) recorded history of use and (ii) menstrual cycle tracking information.

9. The seat assembly of claim 1, wherein the ECU is configured to monitor historic use of the temperature control unit by a user; and
   the ECU is configured to automatically activate the temperature control unit according to the monitored historic use of the temperature control unit.

10. The seat assembly of claim 1, including an additional temperature control unit;
    wherein the ECU is configured to automatically operate a first actuator connected to the seat base, a second actuator connected to the seat back, the temperature control unit, and the additional temperature control unit to reduce discomfort when in the second state.

11. The seat assembly of claim 10, wherein the ECU is configured to operate the temperature control unit and the additional temperature control unit to provide at least one of heating and cooling to reduce symptoms and/or discomfort associated with sciatica when in the second state.

12. The seat assembly of claim 1, wherein the ECU is configured to receive a discomfort reduction seat position and a normal seat position from a user; and the ECU is configured to automatically move the seat base and the seat back into the discomfort reduction seat position via a first actuator connected to the seat base and/or a second actuator connect to the seat back to reduce discomfort when in the second state.

13. A method of operating a seat assembly, the method including:

receiving information relating to whether a user is in (i) a first state corresponding to dysmenorrhea pain or discomfort, and/or (ii) a second state corresponding to sciatica pain or discomfort;

activating a temperature control unit of the seat assembly to reduce pain or discomfort when said user is in the first state and/or the second state; and actuating a seat back of a seat of the seat assembly to reduce pain or discomfort when said user is in the first state and/or the second state.

14. The method of claim 13, wherein activating the temperature control unit includes operating the temperature control unit to provide a seat surface temperature of at least 37 degrees Celsius at a skin level of said user when in the first state to reduce the dysmenorrhea pain or discomfort.

15. The method of claim 14, wherein actuating the seat back includes automatically reclining the seat back when in the first state to reduce the dysmenorrhea pain or discomfort.

16. The method of claim 13, including automatically activating a PEMF coil assembly when in the first state or the second state.

17. The method of claim 13, including receiving a preferred seat position from said user; and actuating a seat base and the seat back such that the seat is disposed in the preferred seat position to reduce compression in the second state;

wherein actuating the seat base and the seat back includes inducing said user to perform an anti-Lasegue maneuver.

18. The method of claim 17, including receiving, from said user, a memory position for the seat when not in the first state or the second state.

19. The seat assembly of claim 1, including:

a first actuator connected to the seat base and configured to rotate the seat base;

a second actuator connected to the seat back and configured to rotate the seat back; and a third actuator connected to a leg support portion of the seat base and configured to rotate the leg support portion;

wherein the ECU is configured to automatically operate at least one of the first actuator, the second actuator, and the third actuator to induce a user to perform an anti-Lasegue maneuver.

20. A seat assembly, including:

a seat having a seat base and a seat back;

a temperature control unit disposed at least partially in the seat back;

a pulsed electromagnetic field (PEMF) coil assembly disposed at least partially in the seat back; and an electronic control unit (ECU) connected with the temperature control unit;

wherein the ECU is configured to receive an input related to (i) a first state corresponding to symptoms and/or discomfort associated with dysmenorrhea and/or (ii) a second state corresponding to symptoms and/or discomfort associated with sciatica;

the ECU is configured to operate the seat assembly according, at least in part, to the input; and the ECU is configured to automatically activate the PEMF coil assembly to reduce discomfort when in at least one of the first state and the second state.

\* \* \* \* \*